United States Patent [19]

Terada et al.

[11] Patent Number: 5,054,477
[45] Date of Patent: Oct. 8, 1991

[54] NEBULIZER

[75] Inventors: Takao Terada, Higashiosaka; Toshiyuki Kobayashi, Kyoto; Tamio Miyake, Otokuni, all of Japan

[73] Assignee: Omron Tateisi Electronics Co., Kyoto, Japan

[21] Appl. No.: 296,314

[22] Filed: Jan. 10, 1989

Related U.S. Application Data

[63] Continuation of Ser. No. 99,813, Sep. 22, 1987, abandoned.

[30] Foreign Application Priority Data

Sep. 22, 1986 [JP] Japan .................. 61-223997
Sep. 25, 1986 [JP] Japan .................. 61-226595
Feb. 17, 1987 [JP] Japan .................. 61-21909

[51] Int. Cl.5 .................................. A61M 11/00
[52] U.S. Cl. ...................... 128/200.14; 128/200.22
[58] Field of Search ............... 128/200.14, 200.18, 128/200.21, 200.22; 239/338, 343, 370, 390, 396

[56] References Cited

U.S. PATENT DOCUMENTS

| 2,826,454 | 3/1958 | Coanda | 128/200.18 |
|---|---|---|---|
| 2,906,463 | 9/1959 | Curry | 128/200.21 |
| 3,112,884 | 12/1963 | Gilmour | 239/396 |
| 3,302,374 | 2/1967 | Szekely | 128/200.18 |
| 3,762,409 | 10/1973 | Lester | 128/200.14 |
| 3,836,079 | 9/1974 | Huston | 128/200.18 |

FOREIGN PATENT DOCUMENTS

| 692821 | 11/1966 | Belgium . | |
|---|---|---|---|
| 2331525 | 1/1974 | Fed. Rep. of Germany . | |
| 3238149 | 4/1984 | Fed. Rep. of Germany . | |
| 777286 | 2/1935 | France | 128/200.21 |
| 675524 | 7/1952 | United Kingdom | 128/200.18 |

Primary Examiner—Edgar S. Burr
Assistant Examiner—Aaron J. Lewis
Attorney, Agent, or Firm—Fish & Richardson

[57] ABSTRACT

A nebulizer comprising a housing having a liquid reservoir at a lower portion thereof and an atomizer space and an atomized liquid discharge port both communicating with the liquid reservoir at an upper portion thereof, a compressed air introduction pipe formed with a nozzle at an end thereof and a liquid suction pipe for sucking liquid in the liquid reservoir, both pipes being provided at a lower portion of the housing, wherein said liquid suction pipe is removably fitted to said compressed air introduction pipe, and a gap between said compressed air introduction pipe and said liquid suction pipe is used as a liquid suction passage.

8 Claims, 13 Drawing Sheets

PRIOR ART

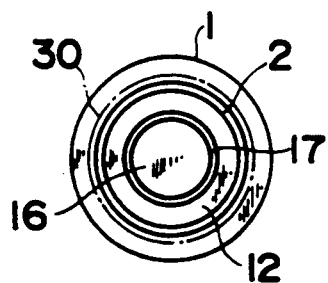
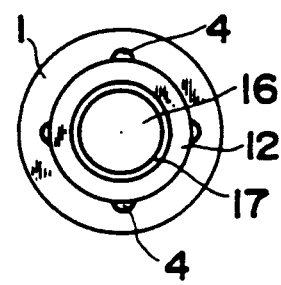
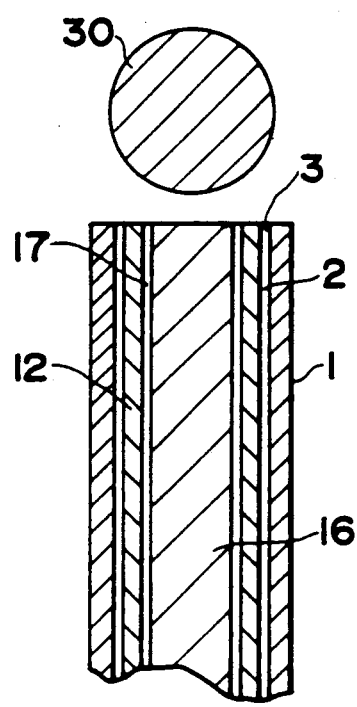

NEBULIZER

This application is a continuation of U.S. application Ser. No. 099,813, filed Sept. 22, 1987 now abandoned.

BACKGROUND OF THE INVENTION

1. Field of the Invention

The present invention relates to a nebulizer for atomizing a liquid, for instance, for nebulizining a medical liquid against a throat.

2. Description of the Prior Art

Conventionally, there are various nebulizers of different types. FIGS. 1a to 1c are cross-sectional views showing the essential portion of the prior-art nebulizers.

The construction of the nebulizer shown in FIG. 1a is such that a compressed air introduction pipe 101 is provided so as to pass through a side wall of a housing 100, and an end of a suction pipe 104 whose base end is put in a liquid reservoir 103 is positioned near a nozzle 102 formed at an end of the compressed air introduction pipe 101. Further, although being the same as in FIG. 1a, the construction of the nebulizer shown in FIG. 1b is such that a baffle 106 is disposed near both ends of the nozzle 102 and the liquid suction pipe 104. Further, in the nebulizer shown in FIG. 1c, a single or plural small-diameter liquid suction passages (pipes) 108 are formed at the outer circumference of a compressed air introduction pipe 107 integral therewith.

In use, a pressure pump connected to the compressed air introduction pipe is driven to obtain a jet stream through the nozzle, in every nebulizer. In this operation, a vacuum generated near the nozzle sucks a liquid in the liquid suction pipe (or passages) toward the nozzle on the basis of vacuum eject action. The liquid sucked upward is mixed with the jet stream, collides against the baffle, and is atomized before discharged outside through an atomized liquid discharge part of the housing.

In the prior-art nebulizers as described above, since the liquid suction pipe or passages are small in diameter, there exist drawbacks in that the liquid suction pipe is subjected to clogging due to crystals of medical liquid or coarse dirt particles.

In addition, in the prior-art nebulizers, since the liquid suction pipe is formed integral with the housing or the liquid suction passage is formed integral with the compressed air introduction pipe, it is very difficult to clean the clogged liquid suction pipe or passages, thus obstructing a safe nebulization. Further, in the case of a nebulizer in which the liquid suction passages are formed integral with the compressed air introduction pipe, there exist other problems such that the forming process is complicated, thus resulting in higher manufacturing cost and complicated repair work in case of nebulizer trouble.

SUMMARY OF THE INVENTION

The primary object of the present invention is to provide a nebulizer of high atomization efficiency without being subjected to clogging in the liquid suction pipe, thus improving user's convenience.

Another object of the present invention is to provide a nebulizer of higher atomization efficiency by allowing scattered atomized liquid to smoothly move toward an atomized liquid discharge port, after liquid-gas mixture collides against the baffle into atomized liquid.

Further, another object of the present invention is to provide a nebulizer of variable atomized liquid rate type such that a quantity of atomized liquid can be adjusted.

To achieve the above-mentioned primary object, the nebulizer of the present invention is constructed as follows:

In a nebulizer in which a compressed air introduction pipe formed with a nozzle at an end thereof and a liquid suction pipe for sucking liquid in a liquid reservoir are provided for a housing including the liquid reservoir at the lower portion thereof and an atomizing space and an atomized liquid discharge port communicating with the liquid reservoir at the upper portion thereof, the liquid suction pipe is removably fitted to the compressed air introduction pipe and further a gap between the compressed air introduction pipe and the liquid suction pipe is constructed as a liquid suction passage.

In the nebulizer constructed as described above, both the compressed air introduction pipe and the liquid suction pipe are formed separately but removably fitted to each other. Therefore, the liquid suction passage formed between the two fitted compressed air introduction pipe and liquid suction pipe can be formed into an annular shape, for instance, so that the volume of the liquid suction passage can be increased, thus eliminating a possibility of clogging in the liquid suction pipe. Further, even if the liquid suction passage is clogged, when the liquid suction pipe is removed from the compressed air introduction pipe, it is possible to readily clean the liquid suction passage, that is, repair the clogged liquid suction passage.

The other features of the present invention will be more clearly appreciated from the following description of embodiments with reference to the attached drawings.

BRIEF DESCRIPTION OF THE DRAWINGS

FIG. 8a is an enlarged cross-sectional view showing the essential portion of still further modification of the fitting condition between the compressed air introduction pipe and the liquid suction pipe, FIG. 8b is a plan view showing the same modification:

FIG. 9 is a plan view showing still another modification of the liquid suction pipe;

DETAILED DESCRIPTION OF THE PREFERRED EMBODIMENTS

Figure 1A:
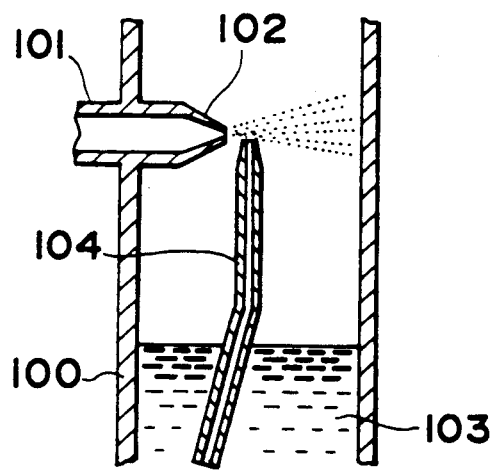
FIGS. 1a, 1b and 1c are cross-sectional views showing the essential portions of prior-art nebulizers.
Figure 1B:
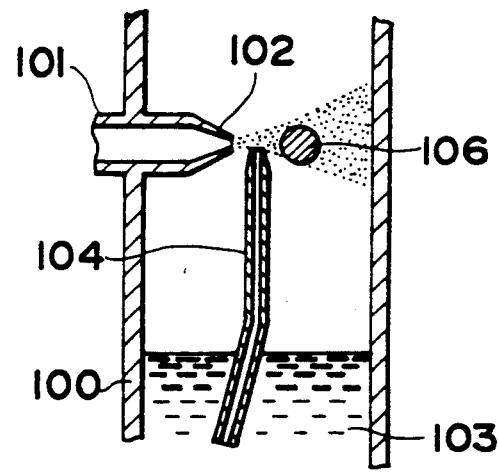
Figure 1C:
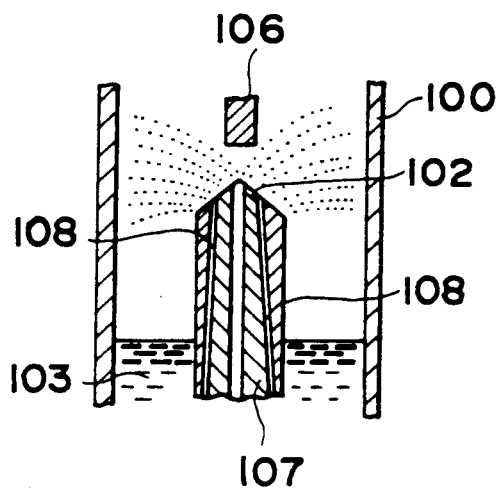
Figure 2:
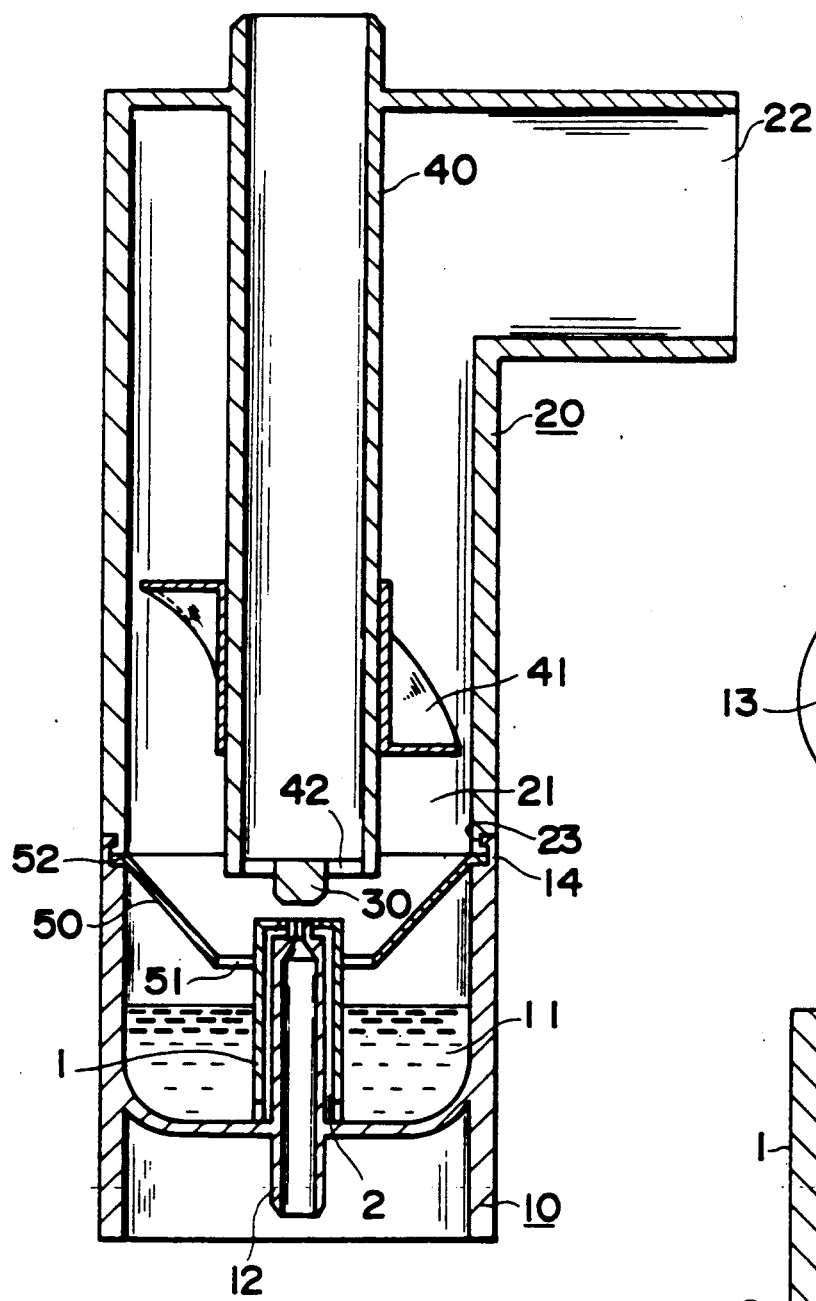
FIG. 2 is a longitudinal cross-sectional view showing the structure of a first embodiment of a nebulizer of the present invention.
Figure 4:
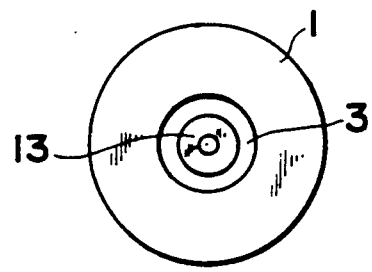
FIG. 4 is an enlarged plan view showing the same jet stream forming section.
Figure 3:
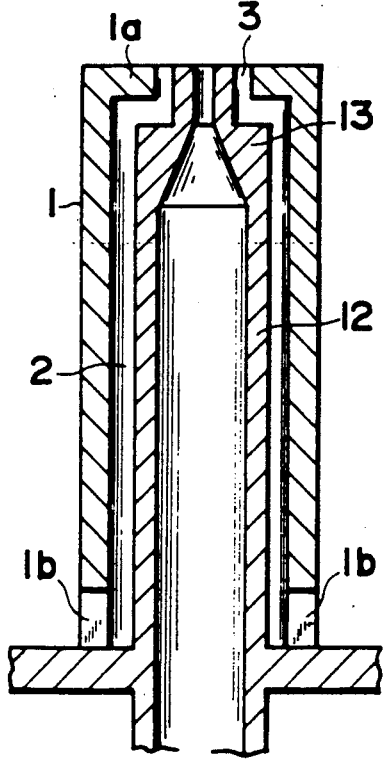
FIG. 3 is an enlarged cross-sectional view showing a jet stream forming section of the first embodiment, which illustrates a fitting condition between a compressed air introduction pipe and a liquid suction pipe.

FIGS. 2 to 4 show the first embodiment of the present invention. With reference to these drawings, the nebulizer comprises a cylindrical lower housing (bottle 10) formed with a liquid reservoir space 11 at the lower portion thereof and a cylindrical upper housing 20 formed with an atomization space 21 at the lower portion thereof and with an atomized liquid discharge space 22 at the upper portion thereof. These two upper and lower housings 20 and 10 are removably fitted to each other via two fitting portions 23 and 14 formed at the lower and upper ends thereof, respectively.

At the bottom wall of the lower housing 10, that is, at the bottom wall of the liquid reservoir space 11, a cylindrical compressed air introduction pipe 12 is disposed integral with the lower housing 10 so as to pass through the center of the bottom wall in the axial direction thereof. This compressed air introduction pipe 12 is formed with a nozzle 13 at its top end thereof, and the lower end of the pipe 12 projecting from the bottom wall of the liquid reservoir space 11 is connected to a pressure pump (not shown) via a tube.

Further, an external air introduction pipe 40 is formed integral with the upper housing 20 so as to pass through the center of the housing 20. This external air introduction pipe 40 is disposed in such a way that the upper end of the pipe 40 projects outward from a bent upper end wall of the upper housing 20 and the lower end thereof is located in the vicinity of the end portion (nozzle 13) of the compressed air introduction pipe 12. A baffle 30 is attached to the lower end of this external air introduction pipe 40 via radial (e.g. cross-shaped) ribs 42. The baffle 30 of this embodiment is cylindrical in shape and chamfered at the circumference of the end thereof.

Further, spiral blades 41 are provided for the lower circumferential surface of the external air introduction pipe 40. When atomized liquid collides against this blades 41, large-diameter atomized liquid particles stick upon the blades 41 and only small-diameter atomized liquid particles are fed to the atomized liquid discharge port 22.

The feature of this embodiment of the nebulizer is to removably and fittably provide the liquid suction pipe 1 to the compressed air introduction pipe 12.

The liquid suction pipe 1 is formed with an inner diameter larger than an outer diameter of the compressed air introduction pipe 12, with an open lower end surface, and with a flange 1a extending inward and having an aperture (hole 3) at the center thereof at the upper end surface of the pipe 1. Further, there are formed a plurality of liquid charge holes 1b at the lower end of the liquid suction pipe 1.

Under the condition that this liquid suction pipe 1 is fitted to the compressed air introduction pipe 12, an annular (in cross section) gap is formed between the inner circumferential surface of the liquid suction pipe 1 and the outer circumferential surface of the introduction pipe 12 so as to serve as a liquid suction passage 2. This liquid suction passage 2 extends to the upper portion of the liquid suction pipe 1, surrounding the nozzle 13, and reaches the hole 3. The hole 3 and the end of the nozzle 13 are located so as to confront the baffle 30 at a predetermined distances.

Further, a dish-shaped fixing member 50 is provided at the outer circumference of this liquid suction pipe 1 integral with the pipe 1. An outer circumferential flange 52 of the fixing member 50 is supported between the fitting portions 23 and 14 of the upper and lower housings 20 and 10. The inside end of the fixing member 50 is formed into radial ribs 51 with spaces between rib members.

Without forming the liquid charge port 1b at the lower end of the liquid suction pipe 1, it is also possible to form a gap between the lower end of the liquid suction pipe 1 and the bottom surface of the liquid reservoir space 11 when the suction pipe 1 is supported by the fixing member 50 so that liquid in the reservoir space 11 can flow into the liquid suction passage 2 through this gap.

Figure 5B:
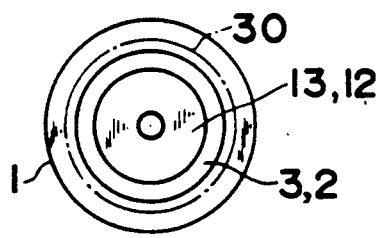
FIG. 5b is a plan view showing the same modification.
Figure 5A:
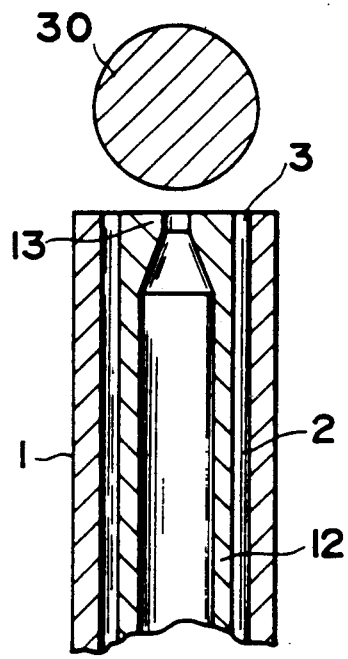
FIG. 5a is an enlarged cross-sectional view showing the essential portion of modification of the fitting condition between the compressed air introduction pipe and the liquid suction pipe.

FIG. 5a is a cross-sectional view showing the essential portion of another modification of fitting condition between the compressed air introduction pipe 12 and the liquid suction pipe 1, and FIG. 5b is the plan view thereof.

In this modification, the liquid suction pipe 1 is formed into a cylinder having upper and lower openings, and the compressed air introduction pipe 12 is provided with no stepped portion at the nozzle portion. In this modification as in the first embodiment, an annular liquid suction passage is formed. Further, a spherical baffle 30 is incorporated.

Figure 6:
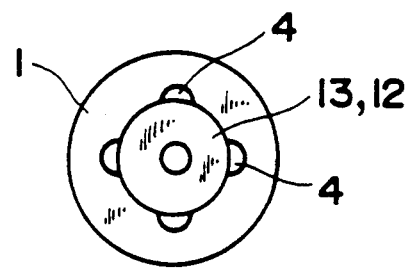
FIG. 6 is a plan view showing another modification of the liquid suction pipe.

FIG. 6 shows a modification of the liquid suction passage. In this example, the inner diameter of the liquid suction pipe 1 is nearly equal to the outer diameter of the compressed air introduction pipe 12, and four grooves 4 are formed at the inner circumferential surface of the liquid suction pipe 1. Therefore, when the liquid suction pipe 1 is fitted to the compressed air introduction pipe 12, these grooves 4 arranged in circular shape serve as the liquid suction passage.

Figure 7:
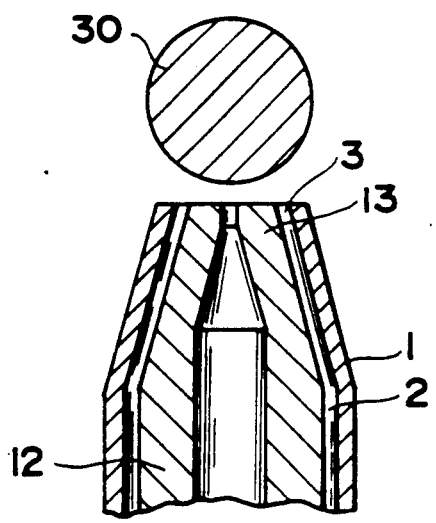
FIG. 7 is an enlarged cross-sectional view showing the essential portion of further modification of the fitting condition between the compressed air introduction pipe and the liquid suction pipe.

FIG. 7 is a cross-sectional view showing still another modification of the fitting condition between the compressed air introduction pipe 12 and the liquid suction pipe 1.

In this example, the compressed air introduction pipe 12 is formed with a tapered end; in the same way, the liquid suction pipe 1 is also formed with a tapered end. That is, the liquid suction passage is narrowed in the upward direction.

FIG. 8a is a cross-sectional view showing further modification of the fitting condition between the compressed air introduction pipe 12 and the liquid suction pipe 1, and FIG. 8b is its plan view.

In this example, a rod 16 is disposed at the center of the compressed air introduction pipe 12 to which the liquid suction pipe 1 is fitted, and an annular space between the outer periphery of the rod 16 and the compressed air introduction pipe 12 is used as a compressed air passage 17. Therefore, in this example, the compressed air passage 17 and the liquid suction passage 2 are both annular in shape. The upper end of the compressed air introduction pipe 12 functions as a nozzle.

FIG. 9 is a plan view showing still another modification of the liquid suction pipe 1. In this example, the liquid suction pipe 1 is formed with a plurality (e.g. 4) of grooves 4 at the inner circumferential surface thereof. When fitted to the compressed air introduction pipe 12, the grooves 4 between the compressed air introduction pipe 12 and the liquid suction pipe 1 become the liquid suction passage. Therefore, in this example, the liquid suction passage is not annular in shape but arranged intermittently in a circular.

Figure 10B:
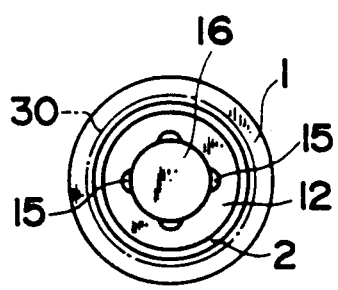
FIG. 10b is a plan view of the same modification.
Figure 10A:
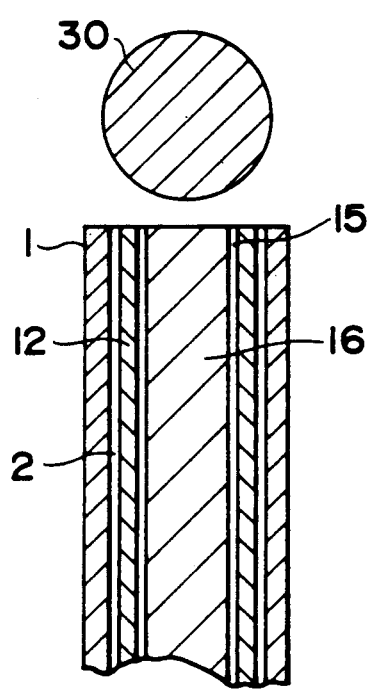
FIG. 10a is an enlarged cross-sectional view showing the essential portion of other modification of the fitting condition between the compressed air introduction pipe and the liquid suction pipe.

FIG. 10a is a cross-sectional view showing still further modification of the fitting condition between the compressed air introduction pipe 12 and the liquid suction pipe 1, and FIG. 10b is its plan view.

In this example, the compressed air introduction pipe 12 is formed with 4 grooves 15 extending in the axial direction thereof and along the inner circumferential surface thereof. A rod 16 having an outer diameter equal to an inner diameter of the compressed air introduction pipe 12 is fitted to the pipe 12, and a gap formed between the rod 16 and the compressed air introduction pipe 12, that is, the grooves 15 function as a compressed air passage. Therefore, in this example, the compressed air passage is arranged intermittently in a circle. On the other hand, a liquid suction passage 2 formed between the liquid suction pipe 1 and the compressed air introduction pipe 12 is annular in shape.

Figure 11:
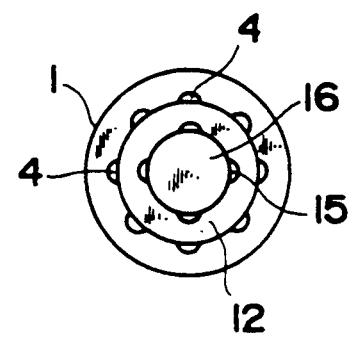
FIG. 11 is a plan view showing other modification of the liquid suction pipe.

FIG. 11 is a plan view showing further modification of the liquid suction pipe 1. In this example, a number of grooves 4 are formed in the inner circumferential surface of the liquid suction pipe 1, and a gap between the pipe 1 and the outer circumferential surface of the compressed air introduction pipe 12 is the liquid suction passage when the pipe 1 is fitted to the pipe 12. Therefore, in this example, the plural compressed air passages and the plural liquid suction passages are both arranged intermittently in concentric positional relationship in plural circles.

In the nebulizer of the first embodiment shown in FIGS. 2 to 4 (including the modifications shown in FIGS. 5a to 11), when the pressure pump is driven, compressed air changes into a jet stream through the nozzle and directly collides against the baffle 30, so that the direction of the stream is converted into the radial direction. Owing to a vacuum generated at this moment, liquid in the liquid suction passage 2 rises in the passage 2 on the basis of vacuum eject action, and directly collides against the baffle 30 through the liquid eject hole 3. Further, liquid atomized by collision against the baffle 30 is discharged from the atomization space 21 to the outside through the atomized liquid discharge port 22 together with the radially scattered air stream.

In this embodiment, therefore, liquid and air stream are jetted and collide against the baffle separately, being different from the prior-art nebulizer in which liquid sucked by a vacuum is immediately mixed with the jet stream and collides against the baffle, so that the atomization efficiency is high, and very small noise is produced (in the prior art, relatively large noise is produced when a mixture of liquid and air stream collides against the baffle), thus enhancing the convenience in use.

In the nebulizer of the first embodiment as described above, since the liquid suction pipe is removably fitted to the compressed air introduction pipe and a gap between the introduction pipe and the suction pipe is used as a liquid suction passage, the liquid suction passage is large in volume and in diameter. Therefore, even if liquid crystals or dust included in the liquid reservoir comes into the liquid suction passage, the passage may not be clogged. In case the liquid suction passage is clogged by large-diameter dirt particles such as dust, it is possible to easily clean the passage into no clogging condition by simply removing the liquid suction pipe from the compressed air introduction pipe.

Further, in the first embodiment, since the compressed air introduction pipe and the liquid suction pipe are constructed separately, the nebulizer is easy to manufacture and handle without trouble, thus providing a high atomization efficiency and low-costly nebulizer.

In the above-mentioned first embodiment, the baffle is spherical or cylindrical in shape and the diameter thereof is determined larger than that of the jet stream spouting outlet (the opening end of the nozzle 13 and the opening end 3 of the liquid passage 2) of the liquid-gas mixture (jet stream and liquid). Therefore, the gas mixed with liquid collides against the baffle sphere 30 and in scattered toward the radial direction. However, part of the atomized liquid scattered radially is obstructed by the surface of the large-diameter baffle sphere 30 and therefore drops toward the liquid reservoir 11 (downward) without flowing toward the atomized liquid discharge port 22 (upward), thus lowering the atomization efficiency.

Figure 13:
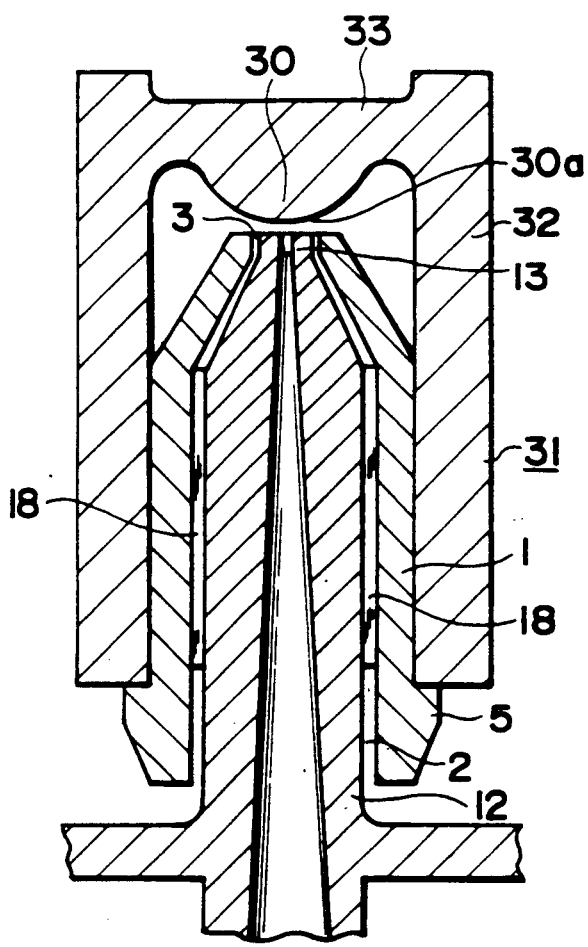
FIG. 13 is an enlarged cross-sectional view showing a part provided with a baffle of the second embodiment.
Figure 14:
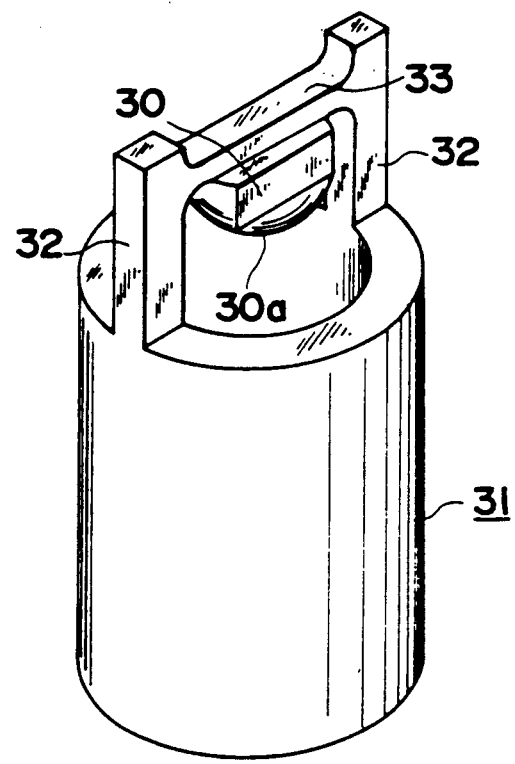
FIG. 14 is a perspective view of the same part.

A second embodiment of the present invention will be described with reference to FIGS. 12 to 14, to solve the above-mentioned problem. In these drawings, the same parts or elements as in the first embodiment are denoted by the same reference numerals without repeating the description thereof.

Similarly to the first embodiment, the nebulizer is constructed by removably fitting the upper housing 20 and the lower housing 10. An O-ring 25 is disposed between the two fitting portions 23 and 14. Further, a mouth piece 24 is replaceably provided for the upper housing 20.

In the upper housing 20, the upper end of the external air introduction pipe 40 is removably fitted to a mounting cylinder 43 formed integral with the housing 20, and the lower end of the pipe 40 is supported on a baffle support cylinder 31. The mounting cylinder 43 opens to a part of the housing 20 (an opening 43a). This opening 43a is adjustably opened or closed by an external air introducing open/close shutter 44 slidably disposed on the housing 20.

The compressed air introduction pipe 12 formed integral with the lower housing 10 at the bottom of the housing 10 and the liquid suction pipe 1 fitted to the pipe 12 are both formed in taper shape at the upper portion thereof in the same way as shown in FIG. 7.

On the outer circumferential surface of the compressed air introduction pipe 12, some ribs 18 (e.g. 4 ribs spaced at 90 degrees) extending axially at the middle of the height of the pipe 12 are formed integral with the pipe 12 to support the fitted liquid suction pipe 1 and form a gap serving as a liquid suction passage 2 between the two.

There exists a gap between the lower end of the liquid suction pipe 1 and the bottom surface of the liquid reservoir 11, so that liquid in the liquid reservoir space 11 flows into the liquid suction passage 2 through this gap. Further, a flange 5 projecting outward is provided at the lower portion of the outer circumference of the liquid suction pipe 1. By this flange 5, the cylinder 31 for supporting the baffle 30 (described below) is fittably supported.

The feature of this embodiment is to form the baffle 30 into a special shape to increase discharge efficiency of the liquid-gas mixture (atomized liquid) colliding against the baffle.

In the support cylinder 31 having upper and lower openings and an inner diameter nearly equal to an outer diameter of the liquid suction pipe 1, the baffle 30 is formed integral with the cylinder 31 under the middle of an arm portion 33 extending between two support poles 32 projecting upward from the upper end surface of the support cylinder 31. That is, the baffle 30 is provided so as to project downward from the middle lower surface of the arm 33. This baffle 30 is formed into a narrow-width rectangular parallelepiped in shape and formed with a projection having a curved surface 30a at the lower portion thereof. The shape of this baffle 30 is the same as that formed by vertically cutting a spherical baffle (sphere) at two positions in parallel to the longitudinal central line so as to have a predetermined width. Therefore, a part of spherical surface (curved surface) is retained on the lower surface thereof. In other words, in this embodiment, the width and length of the baffle 30 are determined so as to correspond to a diameter of the jet stream spouting outlet (the end of the nozzle 13 and the opening 3 of the liquid suction passage) of the liquid-gas mixture. Further, the curved portion 30a extends in the longitudinal and width directions.

The support cylinder 31 formed with such baffle 30 is removably fitted to the liquid suction pipe 1, and the lower end of the support cylinder 31 is supported by the flange 5 of the liquid suction pipe 1. Under these fitted conditions, the baffle 30 is located a little over the top end of the nozzle 13 of the compressed air introduction pipe 12 and the opening 3 of the liquid suction passage 2.

In the nebulizer thus constructed, compressed air is jetted through the nozzle 13 in the form of jet stream, and a vacuum generated near the opening 3 of the liquid suction passage 2 due to this jet stream moves liquid upward in the liquid suction passage 2 on the basis of vacuum eject action, and jets the liquid from the passage opening 3. Further, the jetted liquid and stream collide against the baffle 30 positioned over the nozzle 13 and opening 3 into atomization.

The liquid-gas mixture collides against the central portion of the curved surface 30a of the baffle 30 positioned at right angles with respect to the jet direction. At this operation, since the width of the baffle 30 is narrow, the atomized liquid scattered in the radial directions rises upward without being subjected to any obstruction. Further, since the collision surface is curved, the atomized liquid can smoothly move upward along the curved surface 30a. Therefore, almost all the atomized liquid flows upward (toward the atomized liquid discharge port 22) without dropping downward (toward the liquid reservoir space 11), thus improving the discharge rate of the atomized liquid.

In the nebulizer according to the second embodiment, within the housing provided with the liquid reservoir space at the lower portion thereof and the atomizing space and atomized liquid discharge port both communicating with the liquid reservoir space at the upper portion thereof, there are disposed the compressed air introduction pipe having a nozzle at an end thereof, the liquid suction pipe for supplying liquid in the liquid reservoir, and the baffle positioned so as to face the nozzle of the compressed air introduction pipe and the passage opening of the liquid suction pipe, and the baffle is formed in such a way that the lower projecting surface of the narrow rectangular parallelepiped is curved.

In the nebulizer thus constructed, the baffle is rectangular in shape and curved at the lower portion; that is, baffle is formed small in shape as compared with the jet stream spouting outlet of the liquid-gas mixture (the nozzle opening end and liquid suction passage opening). Therefore, liquid-gas mixture jetted from the nozzle end of the compressed air introduction pipe and the liquid suction passage opening of the liquid suction pipe both collide against the curved surface positioned perpendicular to the jet stream direction and scattered. In this moment, since the width of the baffle is narrow, the atomized liquid colliding against the curved surface can smoothly move upward along the curved surface without being subjected to any obstruction, thus improving the atomization efficiency.

Figure 12:
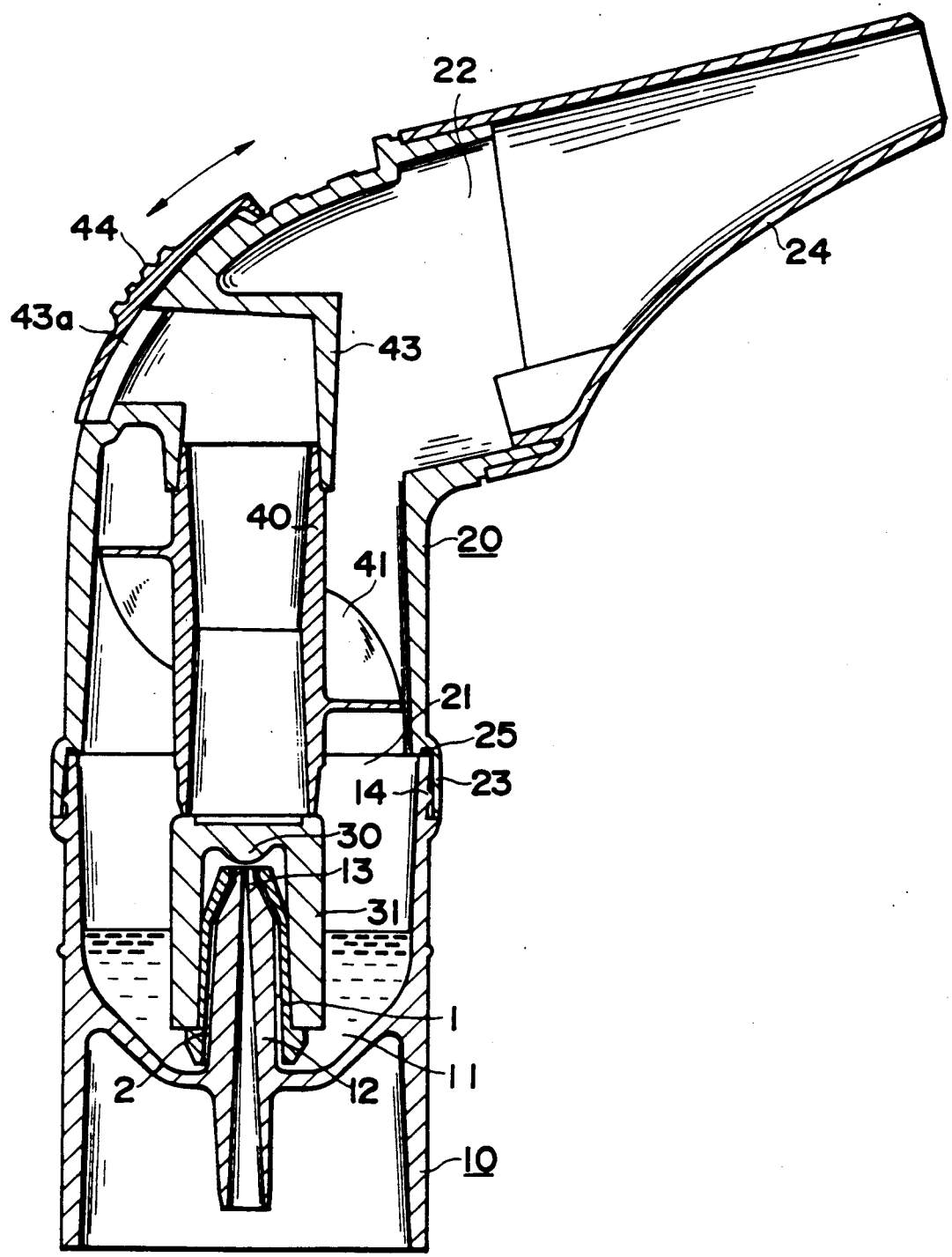
FIG. 12 is a longitudinal cross-sectional view showing the construction of a second embodiment of the nebulizer of the present invention.

In the nebulizer according to the second embodiment shown in FIG. 12, in order to adjust the quantity (rate) of atomized liquid, the amount of air introduced inside is adjusted by adjustably opening/closing the external air charge opening 43a of the external air introduction pipe 40, 43, so that the amount of atomized liquid discharged from the discharge port can be adjusted by substantially changing the power (flow rate) of the atomized liquid.

Therefore, there exist some drawbacks as follows:

(1) Although a change in the amount of atomized liquid depends upon a change in the amount of air to be introduced, since the amount of air introduced is greatly dependent upon a difference in pressure between the inside and the outside of the nebulizer, not upon the area of the air inlet part, as long as the air inlet is open a little, it is impossible to change the pressure difference effectively by increasing the open area of the air inlet part.

(2) Since the amount of atomized liquid produced in the atomization space does not change sufficiently, but only the amount of atomized liquid discharged outside changes, atomized liquid is stored much inside the nebulizer, thus lowering the efficiency of liquid recovery.

(3) When the air inlet port is closed, the amount of atomized liquid to be discharged extremely decreases.

The third embodiment provided with means for solving the above-mentioned problems will be described hereinbelow in further detail.

Figure 15:
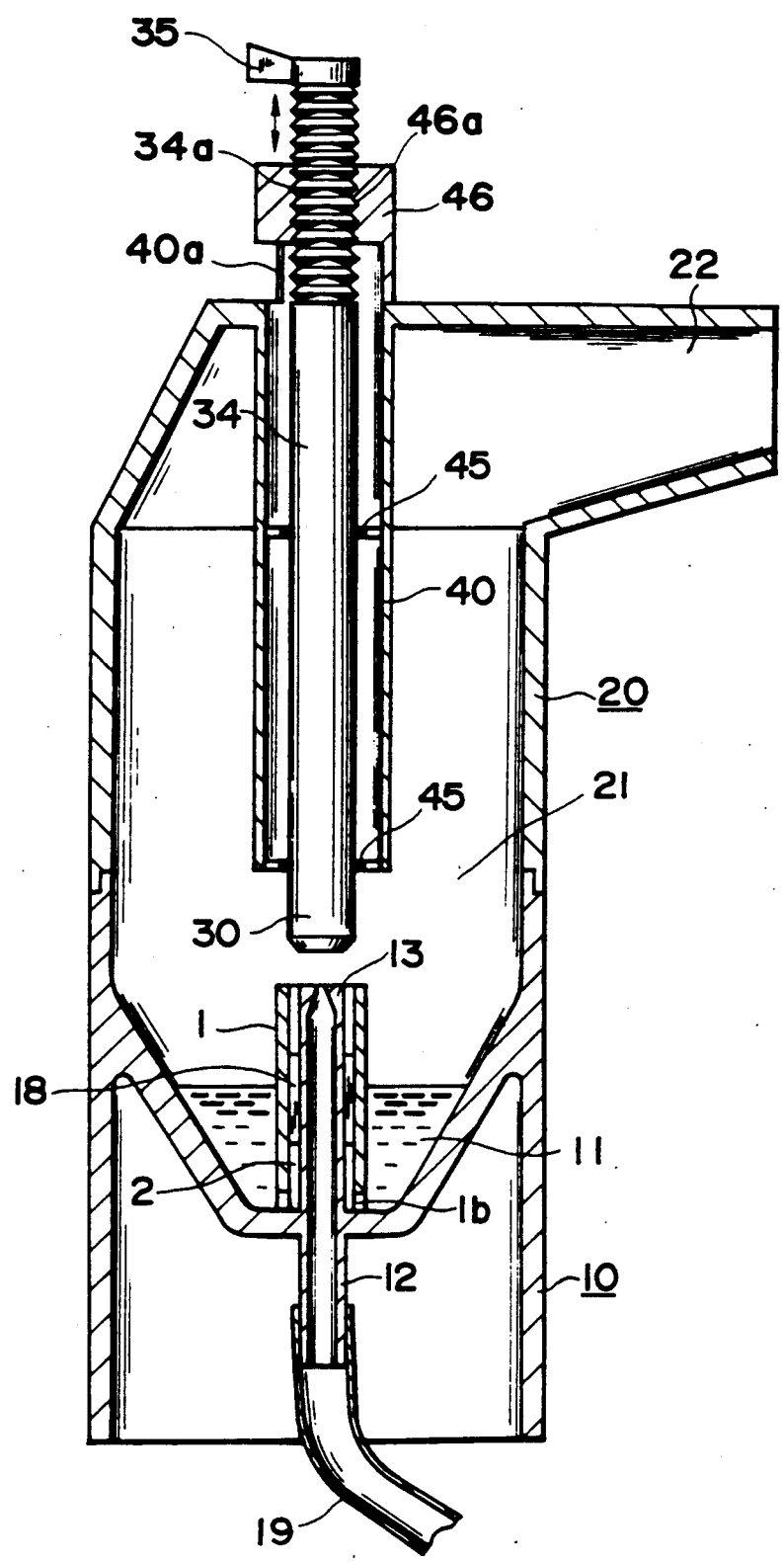
FIG. 15 is a longitudinal cross-sectional view showing a third embodiment of the nebulizer of the present invention.

FIG. 15 shows the third embodiment, in which the same parts or elements explained in the first and second embodiments are denoted by the same reference numerals without repeating the description thereof.

The compressed air introduction pipe 12 and the liquid suction pipe 1 are similar to these shown in FIGS. 5a and 5b. At the outer circumference of the compressed air introduction pipe 12, ribs 18 extending in the axial direction of the pipe 12 and arranged at regular angular intervals are disposed so as to form a gap of the liquid suction passage 2 between the introduction pipe 12 and the suction pipe 1. Further, the liquid suction pipe 1 is supported on the bottom surface of the liquid reservoir space 11, and formed with some liquid inlets 1b at the lower portion thereof. The lower end of the compressed air introduction pipe 12 is connected to a pressure pump (not shown) via a hose 19 so that compressed air is supplied from the pressure pump.

A support member 46 is provided at the upper end of the external air introduction pipe 40 disposed on the upper housing 20. The pipe 40 is formed with a horizontally directing external air inlet 40a at the position under the support member 46 and outside the housing 20. Further, the support member 46 is formed with a threaded hole 46a. A rod 34 is fitted to the external air introduction pipe 40. The upper portion of this rod 34 is threaded at 34a and screwed into the threaded hole 46a in the support member 46 so as to be supported by the support member 46. The lower end of the rod 34 is the baffle 30 the same in shape as in FIG. 2, and this baffle 30 projects from the lowermost end of the external air introduction pipe 40.

A knob 35 is attached to the upper end of the rod 34. Therefore, when this knob 35 is rotated to rotate the rod 34, the lower end of the baffle 30 moves up and down. The rod 34 is supported at the middle and lower positions via two bearings 45. Each bearing 45 is composed of a ring rotatably and slidably fitted to the rod 34 and a radial rib for fixing this ring to the external air introduction pipe 40.

In the nebulizer of the third embodiment, when compressed air is fed to the compressed air introduction pipe 12 via the hose 19, the compressed air is jetted from the nozzle 13 into a jet stream. A vacuum generated by this jet stream raises liquid within the liquid suction pipe 1 (whose level is the same as that of the liquid reservoir space 11) on the basis of vacuum eject action and ejects the liquid upward together with the jet stream. The jet stream mixed with medical liquid collides against baffle 30 disposed on the lower end of the rod 34 and over the nozzle 13. Therefore, the medical liquid is scattered into atomization condition in various directions. On the other hand, since external air is introduced through the external air introduction pipe 40, the atomized liquid is urged upward by the external air pressure within the atomization space 21 surrounding the external air introduction pipe 40, being discharged to the outside through the atomized stream discharge port 22.

When the rod 34 is rotated by moving the knob 35, the baffle 30 disposed at the end of the rod 34 is moved upward or downward, so that a gap between the baffle 30 and the nozzle 13 changes and therefore the amount of atomized liquid can be adjusted.

Figure 16:
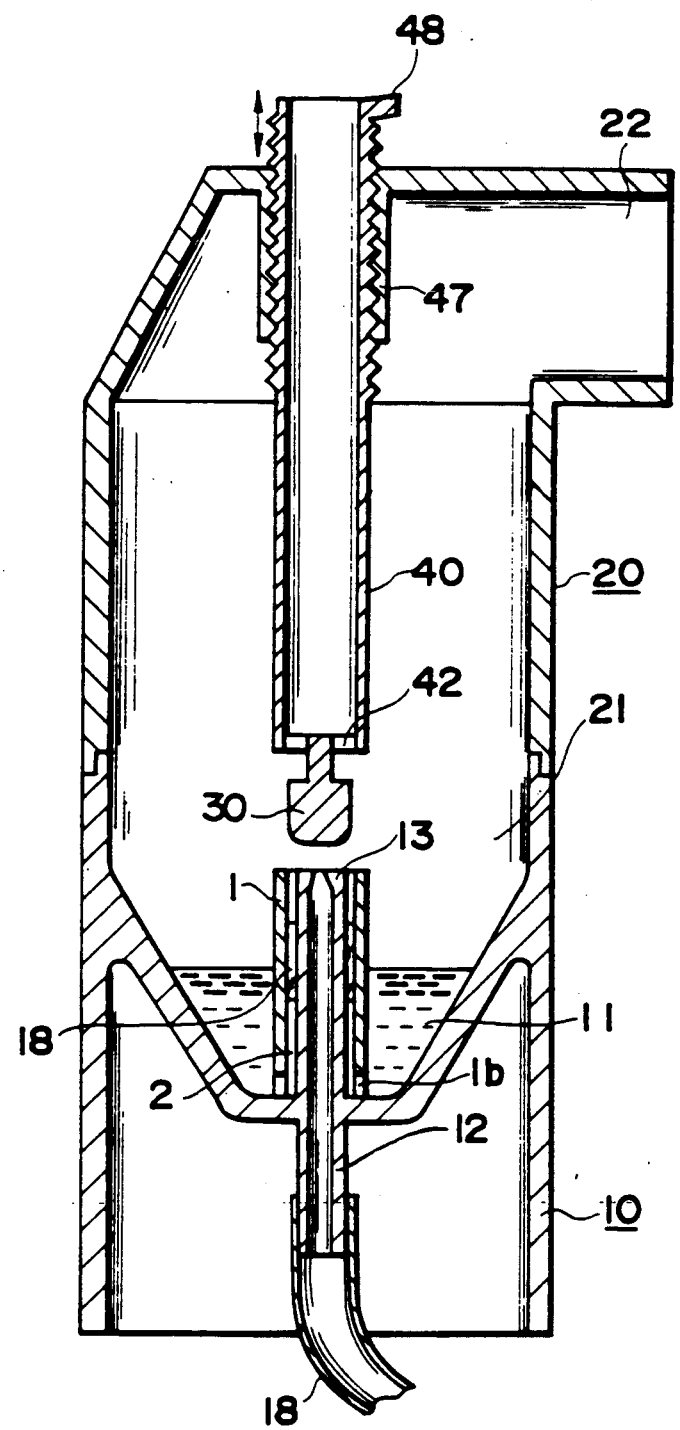
FIG. 16 is a longitudinal cross-sectional view showing a modification of the third embodiment.

FIG. 16 shows a modification. This nebulizer is basically the same as that shown in FIG. 15, the same reference numerals being retained for the same or similar parts which have the same functions.

The features of the modification of the nebulizer is as follows: a cylindrical support member 47 is vertically disposed downward from the top surface of the upper housing 20; the external air introduction pipe 40 is fittably screwed to this cylindrical support member 47; the baffle 30 is disposed at the lower end of the external air introduction pipe 40; when the external air introduction pipe 40 is moved up and down, the baffle 30 is also moved up and down to adjust a distance between the nozzle 13 and the baffle 30. An operation knob 48 is attached to the upper end of the external air introduction pipe 40 for providing an easy adjustment.

The operation of the nebulizer is the same as that shown in FIG. 15.

Figure 17A:
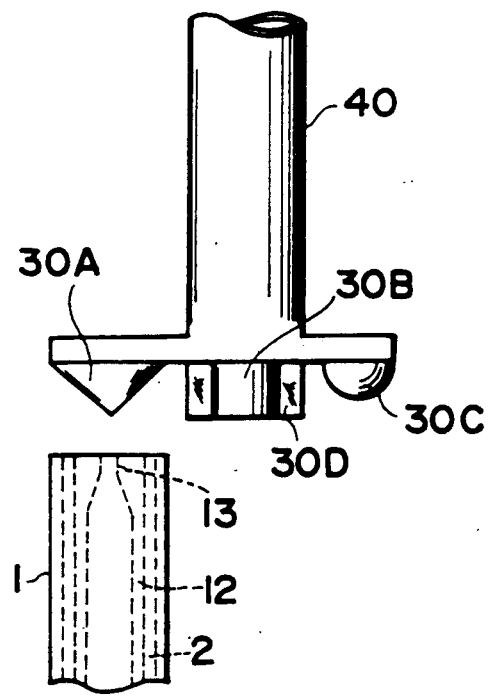
FIG. 17a is a side view showing another modification of the baffle.
Figure 17B:
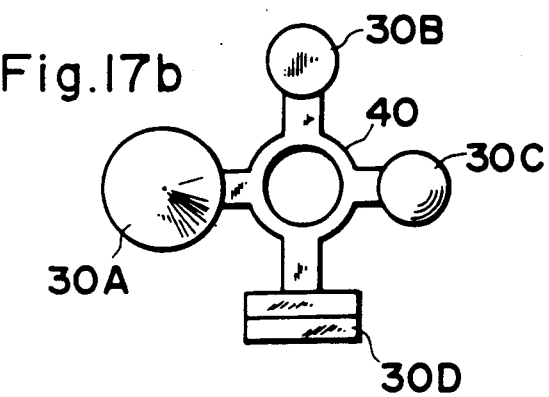
FIG. 17b is a bottom view showing the same baffle.

FIGS. 17a and 17b shows the essential part (baffles) of another modification of the nebulizer. In the nebulizer shown in FIGS. 15 and 16, a single baffle 30 is formed at an end of the external air introduction pipe 40 coaxially and integrally therewith so that the nozzle 13 and the baffle 30 confront each other. In this modification, however, a plurality of baffles 30A, 30B, 30C and 30D are arranged at the end of the external air introduction pipe 40 on a concentric circle larger in diameter than the external air introduction pipe 40; and the compressed air introduction pipe 12 is arranged so that the nozzle 13 thereof is positioned under a point of concentric circle. These baffles are different from each other in shape, in such a way that the baffle 30A is reverse conical; the baffle 30B is cylindrical; the baffle 30C is semispherical; and the baffle 30D is reverse triangular in cross section.

In this nebulizer, when the external air introduction pipe 40 is rotated, a distance between the end of the external air introduction pipe 40, that is, each baffle 30A, 30B, 30C or 30D and the nozzle 13 changes, and simultaneously the kind of baffles confronting the nozzle 13 changes. As already explained, when the distance between the baffle and the nozzle changes, the amount (rate) of atomized liquid changes. In this modification, however, since the baffle confronting the nozzle 13 changes or the shape of the baffle confronting the nozzle 13 changes, so that the diameter of atomized liquid particles changes. That is, in this modification, it is possible to adjust both the amount of atomized liquid and the particle diameter thereof, simultaneously.

Further, it is also possible to provide a plurality of baffles of different shapes on the lower end of the rod 34 shown in FIG. 15, being different from the lower end of the external air introduction pipe 40.

Figure 18:
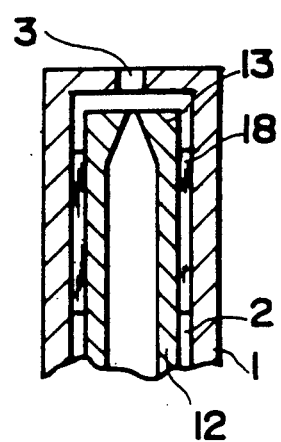
FIG. 18 is a cross-sectional view showing another modification of the jet stream forming section.

FIG. 18 shows a modification of the jet stream generating section. In the drawing, a small air supply opening 3 is formed at the center of the upper surface of the liquid suction pipe 1, and the nozzle 13 is positioned under this opening 3.

In the third embodiment as shown above, the amount of atomized liquid is adjustable according to the distance between the nozzle through which compressed air is jetted and the baffle confronting the nozzle. For doing this, a baffle position adjusting means formed with a baffle at one end thereof and retained by the housing at the other end portion thereof is provided so that the distance between the baffle and the nozzle can be adjusted. When the baffle is moved up and down through this baffle position adjusting means, the distance between the nozzle and the baffle changes, so that the amount of atomized liquid changes and therefore the amount of discharged atomized liquid changes.

Therefore, it is possible to freely adjust the amount of atomized liquid in analog or digital fashion by adjusting the distance between the baffle and the nozzle by actuating the baffle position adjusting means. Further, since the external air introduction pipe is always kept open, as long as the pressure of compressed air jetted from the nozzle does not change, a constant external air can be introduced at all times, so that the power (flow rate) of the atomized liquid to be discharged is kept constant irrespective of the amount of atomized liquid. To adjust the amount of atomized liquid to be discharged, the amount of atomized liquid to be formed is directly controlled (without adjusting the amount of atomized liquid to be discharged from the atomizing space to the outside), it is possible to reduce the amount of atomized liquid to be stored inside, thus improving the liquid atomization efficiency.

Conventionally, an air compressor of bell-diaphragm type has been used for the pressure pump for generating conpressed air to be supplied to the compressed air introduction pipe 12, that is, for the compressor. Further, the nozzle diameter and the opening diameter of the liquid suction passage have been determined on the basis of diaphragm-type compressor characteristics, respectively.

Figure 19:
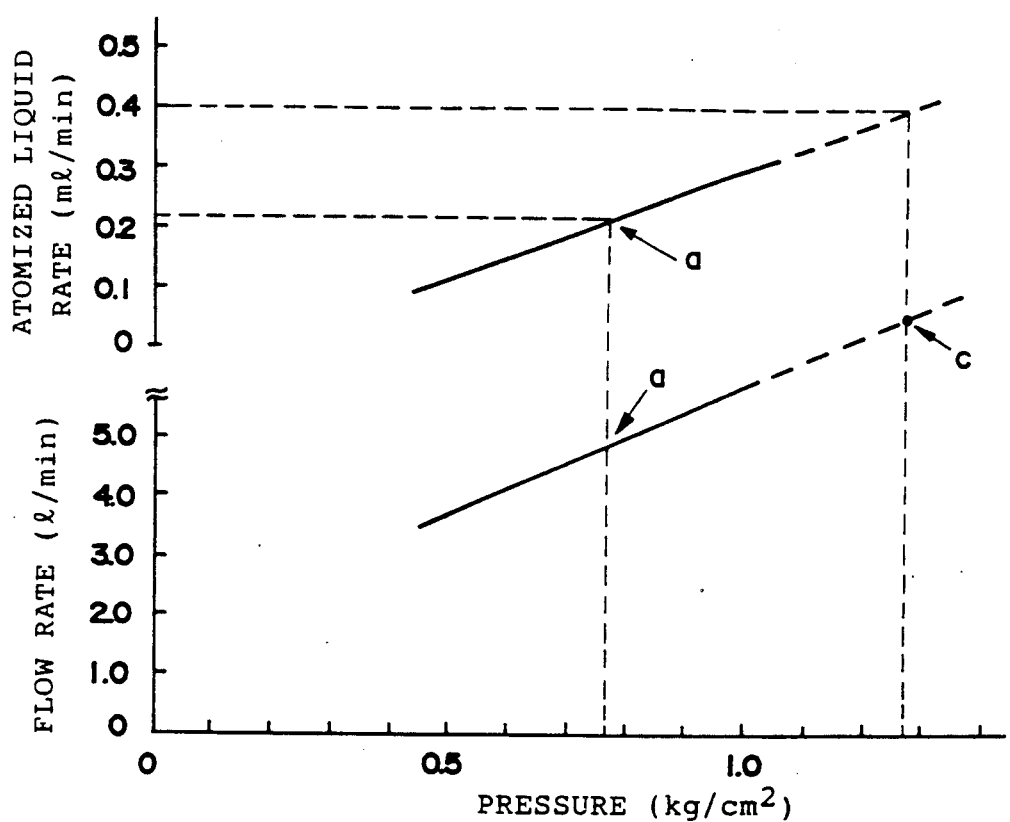
FIG. 19 is a graphical representation showing atomization characteristics of a prior-art diaphragm type compressor.

In the nebulizer, however, it has been known that the pressure when liquid is atomized is universally determined in combination of the atomizing part and the compressor, and the amount of atomized liquid is determined according to the pressure. FIG. 19 shows the mutual relationship between the conventionally adopted diaphragm type air compressor pressure and the amount of atomized liquid (atomizer characteristics).

When the pressure of the diaphragm type air compressor is about 0.75 kg/cm$^2$, the mutual relationship between the atomizer nozzle diameter and the pressure is well satisfied (see arrows a in FIG. 19). The flow rate at this moment is about 5.0 l/min, and the atomized liquid rate corresponding thereto is about 0.2 ml/min. For instance, when the atomized liquid rate is required to increase (e.g. to 0.4 ml/min), it is necessary to use a compressor of flow rate as shown by a black dot in FIG. 19 (an arrow c); that is, a compressor of about 1.3 kg/cm$^2$ pressure.

However, the diaphragm type air compressor provided with these performances is of large-sized pump such that the weight is 4 kg or more and the electric power consumption is 50 W or more. Therefore, the size is large; the electric power consumption is high; and the cost is high. In addition, since a large-sized compressor vibrates much, the noise is as high as 60 dB or more, so that there exists a disadvantages such that it is difficult to install the noisy compressor at a hospital, for instance. Further, since temperature increases 40 degrees or more in this compressor, the compressor is subjected to trouble. In the diaphragm-type air compressor, in particular, the life can be known after the compressor will not move, due to the structural standpoint. Therefore, the maintenance chance is lost, and therefore the nebulizer often stops during operation.

The fourth embodiment provides a nebulizer having a high atomization efficiency by use of a small-sized lightweight compressor.

In brief, the nebulizer of the fourth embodiment is constructed as follows: the nebulizer comprises a nebulizer case provided with a compressor inside and an atomizing cylinder removably connected to the compressor in the nebulizer case via an air feeding tube; the compressor is of linear motor driven free piston type; and the atomizing nozzle diameter of the atomizing cylinder is determined so as to correspond to compressor characteristics.

Figure 20:
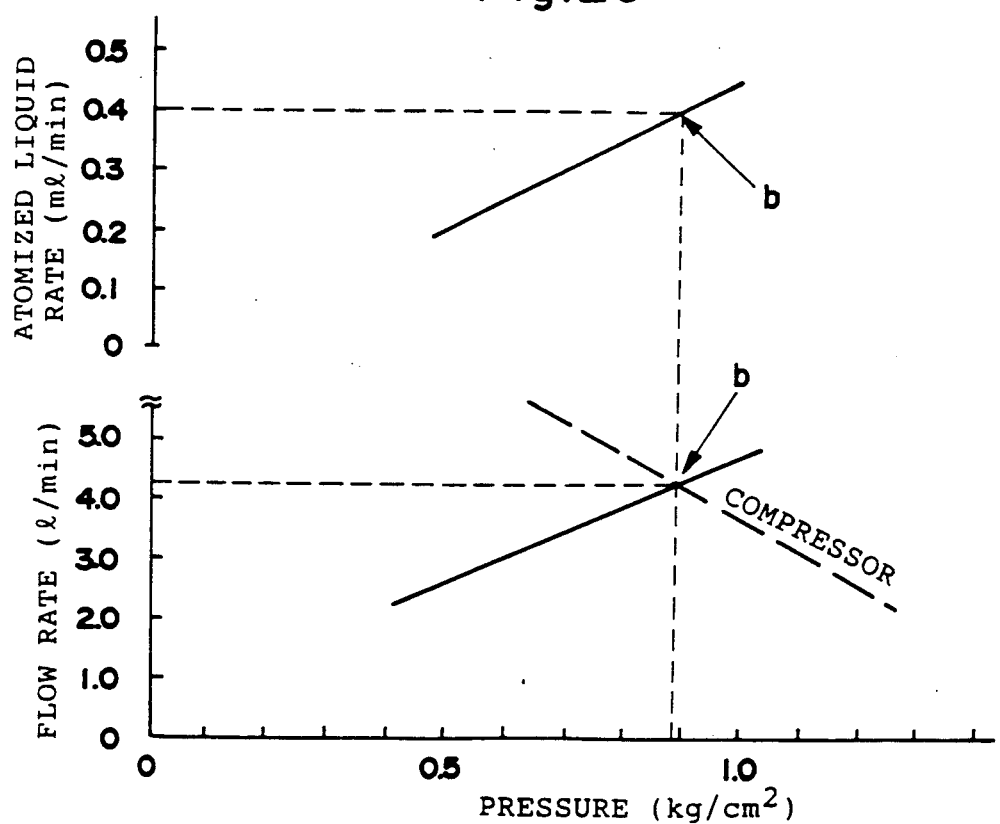
FIG. 20 is a graphical representation showing atomization characteristics of a free-piston type air compressor driven by a linear motor.

In the nebulizer thus constructed, a linear motor driven free piston type air compressor is used, and the atomizing nozzle diameter is determined on the basis of the compressor characteristics. FIG. 20 shows the characteristics of the linear motor driven free piston type air compressor, which indicates that when an atomized liquid rate (4.0 ml/min) twice larger than that of the conventional valve (2.0 ml/min) is required, a compressor whose pressure is about 0.9 kg/cm$^2$ (the flow rate is about 4.0 l/min) is used (see arrows b). The linear motor driven free piston type air compressor with the performance as described above is very small in size, vibration, noise and power consumption, but very high is atomization efficiency.

Figure 21:
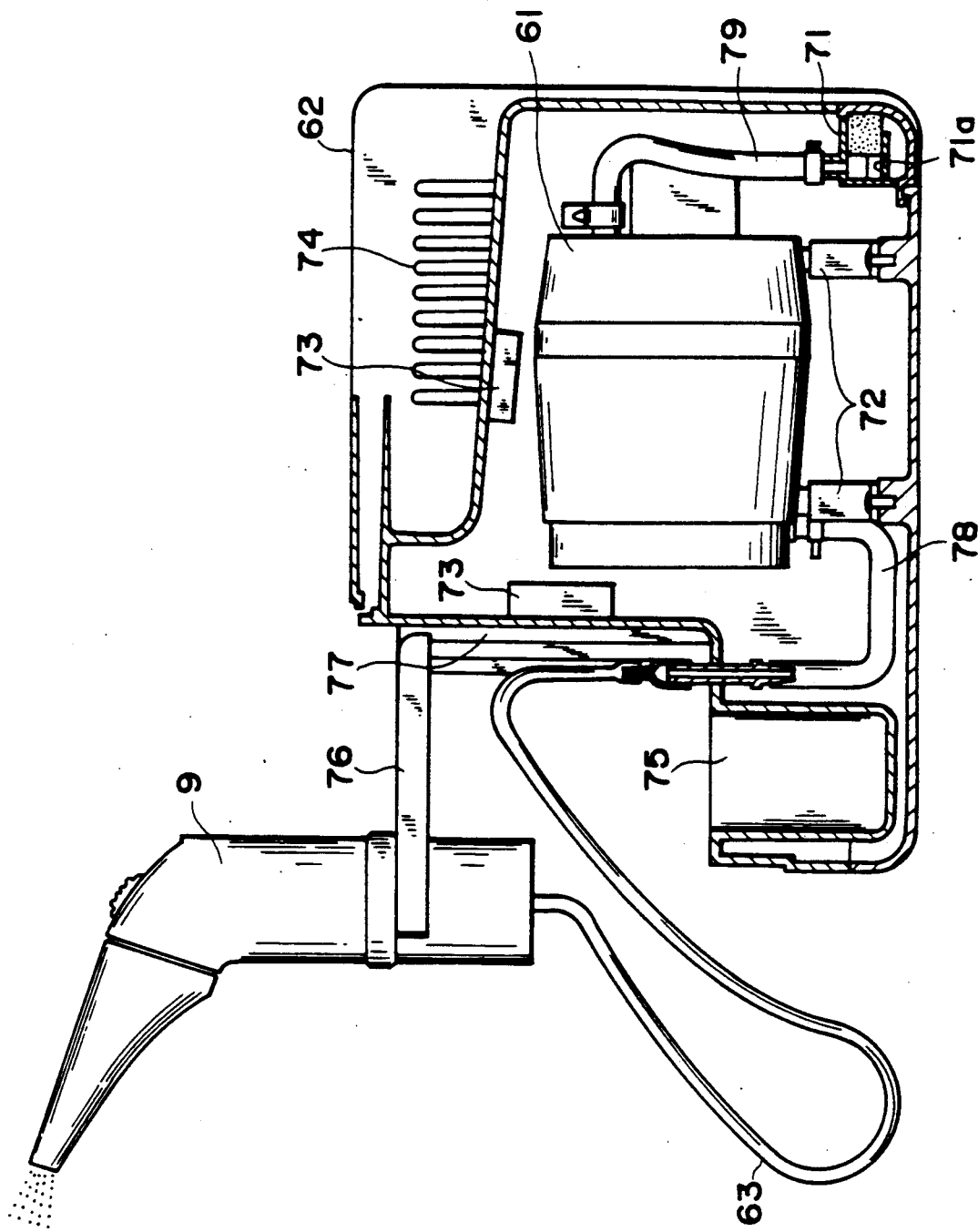
FIG. 21 is a front cross-sectional view showing a part of cross section of a fourth embodiment of the nebulizer of the present invention.

FIG. 21 is a front view, partially cross-section, showing the fourth embodiment of the nebulizer.

The nebulizer comprises a nebulizer case 62 provided with a compressor 61 and a filter housing 71 inside the case and an atomizing cylinder 9 connected to the compressor 61 via an air feeding tube 63.

In the nebulizer housing 62, the compressor (linear motor driven free piston air compressor) 61 described later is mounted on a rubber mounting base 72 at the middle of a box-shaped inner space of the case 62. Some damping members 73 for protecting the compressor 61 from external vibrations or shocks are projectingly provided at both ends and on both side surfacs of the case 62. Further, a plurality of ventilation openings 74 are formed on both side walls of the case 62 to radiate heat therethrough.

Further, on one end wall of the case 62, there are provided an atomizing cylinder housing space 75, an atomizing cylinder support arm 76 for supporting the atomizing cylinder 9 when the cylinder 9 is used and arm setting portion 77 for receiving the support arm 76 when the cylinder 9 is not used.

Further, a discharge tube 78 is connected to the air feed section of the compressor 61. A pipe joint of this discharge tube 78 is fixed to the outside of the case 62 to removably connect the air feed tube 63 connected to the atomizer cylinder 9. Further, a suction tube 79 is connected to the suction section of the compressor 61, and one end of this suction tube 79 is connected to a suction cylinder 71a of the filter housing 71.

The atomizing cylinder 9 is shown in FIG. 12, in which the compressed air introduction pipe 12 is connected to the air feed tube 63. The jet stream spouting part and the baffle of the atomizing cylinder 9 are the same as that shown in FIG. 13, its enlarged view being also shown in FIG. 22.

Figure 22:
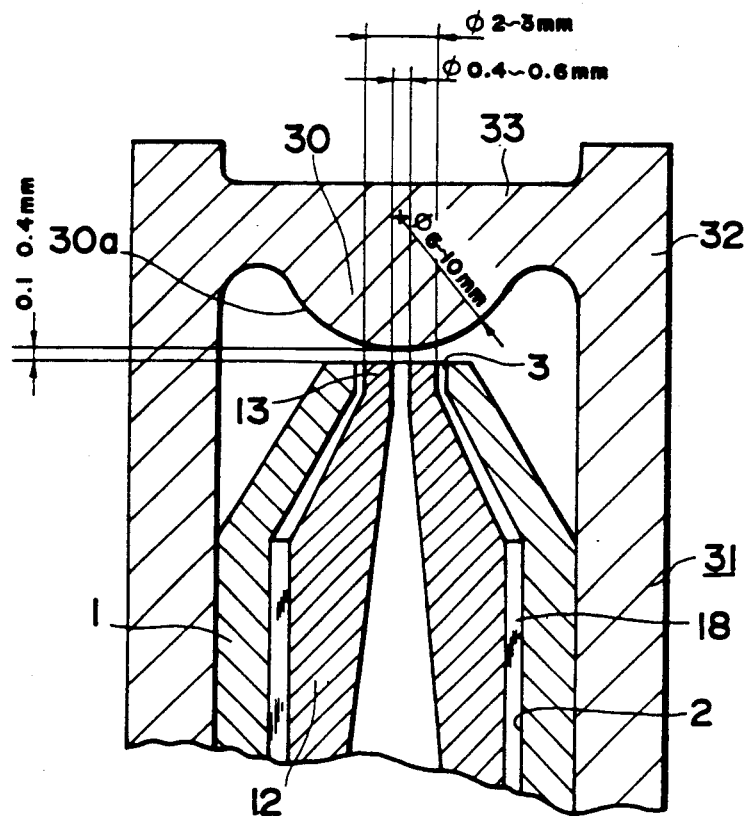
FIG. 22 is an enlarged cross-sectional view showing the relationship between the nozzle and the baffle.

In this embodiment, under due consideration of atomization efficiency, that is, characteristics of the compressor 61 (linear motor driven free piston air compressor), as shown in FIG. 22, a distance between the nozzle 13 and the baffle 30 (the curved surface 30a) is determined to be 0.1 to 0.4 mm; a diameter of the nozzle 13 (jet stream generating aperture diameter) is determined to be 0.4 to 0.6 mm; the outer diameter of the nozzle is determined to be 2 to 3 mm; the curvature of the curved surface 30a of the baffle 30 is determined to be 6 to 10 mm in diameter, in order to improve the atomization efficiency.

Figure 23:
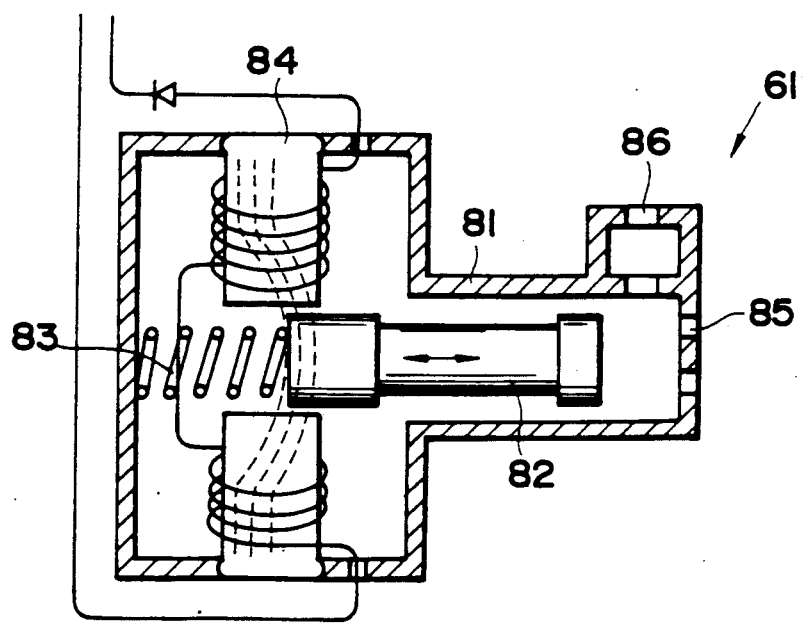
FIG. 23 is an outline of the cross-sectional view showing the construction of the free-piston type air compressor driven by a linear motor.

FIG. 23 is a cross-sectional view diagrammatically showing the structure of a linear motor driven free piston type air compressor 61.

In this air compressor 61, a piston 82 is disposed within a cylinder 81; and a spring 83 is attached to one end of the piston 82 to always urge the piston 82 toward the side of the suction opening 85. On the other hand, an electromagnetic coil 84 is disposed on the base end side (spring disposed side) of the piston 82. When an alternating power supply is rectified into a half wave (positive half wave cycle) by a built-in rectifier and supplied to the electromagnetic coil 84, the electromagnet is actuated to attract the piston 82 against the spring 83, so that air flows from the suction opening 85 into the cylinder 81. In contrast with this, no current flows during negative half-wave cycle without magnetization, so that the attracted piston 82 is returned to the original position by the spring 83. Therefore, air within the cylinder 81 is compressed and discharged from the discharge opening 86. That is, compressed air is fed periodically at a cycle corresponding to the power supply frequency. In this linear motor driven free piston type air compressor 61, the motor unit (piston driving mechanism) and the compressor unit (compressor mechanism) are constructed integral with each other, small in size, light in weight, and further its pressure and flow rate are controllable on the basis of voltage control. Although not shown, valves are provided at the air inlets 85 and the air outlet 86.

In the nebulizer constructed as described above, a linear motor driven free piston type air compressor 61 is used, and the diameter of the atomizer nozzle 13 is determined so as to correspond to the characteristics of compressor 61, as already explained. Therefore, as shown by the atomizer characteristics in FIG. 20, in order to obtain an atomized liquid rate of 0.4 ml/min, for instance, a compressor whose pressure is about 0.9 $kg/cm^2$ (the atomizer flow rate is about 4.0 l/min) is used. The linear motor driven free piston type air compressor 61 of this performance is small in size, light (about 2 kg) in weight, low (20 W) in power consumption, low (about 30 degrees) in temperature rise, little in vibration, and low (40 dB) in noise; as a result, it is possible to drive the compressor quietly. Since the linear motor driven free piston type compressor is used and the atomizer nozzle is determined so as to correspond to the compressor characteristics, it is possible to minimize the compressor while doubling the atomized liquid rate as compared with the conventional type.

In the nebulizer of the fourth embodiment, compressed air is fed from the compressor to the nozzle by means of the linear motor driven free piston type air compressor and the nozzle whose diameter is determined according to the compressor characteristics, it is possible to minimize the size and weight of the nebulizer and to improve the atomizer efficiency.

Since noise, vibration, heat generation, etc. are all minimized, the nebulizer is usable at hospital and home under quiet condition. Further,, since the compressor performance is degraded little by little gradually with increasing lapse of time, it is possible to determine the maintenance time when the nebulizer does not operate satisfactorily. Therefore, it is possible to solve the disadvantages involved in the prior art nebulizer such that nebulizer operation stops suddenly during use.

Further, when the nozzle is clogged, the locking pressure increases and therefore driving current decreases, there exists no danger of heat generation or spontaneous combustion as in the conventional nebulizer.

What is claimed is:

1. A nebulizer, comprising:

a housing having a liquid reservoir located at a lower portion thereof and an atomizer space and an atomized liquid discharge port located at an upper portion thereof, said atomizer space and said atomized liquid discharge port communicating with said liquid reservoir;

a compressed air introduction pipe provided at the lower portion of the housing, said compressed air introduction pipe having a nozzle;

a liquid suction pipe provided at the lower portion of the housing for sucking liquid in the liquid reservoir, said liquid suction pipe being removably fitted to said compressed air introduction pipe so that a liquid suction passage is formed between said liquid suction pipe and said compressed air introduction pipe, said liquid suction passage having an opening;

a baffle support disposed around said liquid suction pipe;

two support poles projecting from said baffle support;

an arm extending between said support poles; and a baffle connected to said arm, said baffle being disposed near the nozzle of the compressed air introduction pipe and the opening of the liquid suction passage, said baffle being formed as a parallelpiped of narrow width with a curved lower surface facing said nozzle and said opening.

2. The nebulizer as claimed in claim 1, further comprising an air tube connected to said compressed air introduction pipe, and a compressor for feeding air to said air tube, wherein said compressor is of a linear motor driven free piston type.

3. A nebulizer, comprising:

a housing having a liquid reservoir located at a lower portion thereof and an atomizer space and an atomized liquid discharge port located at an upper portion thereof, said atomizer space and said atomized liquid discharge port communicating with said liquid reservoir;

a compressed air introduction pipe provided at the lower portion of the housing, said compressed air introduction pipe having a nozzle;

a liquid suction pipe provided at the lower portion of the housing for sucking liquid in the liquid reservoir, said liquid suction pipe being removably fitted to said compressed air introduction pipe so that a liquid suction passage is formed between said liquid suction pipe and said compressed air introduction pipe, said liquid suction passage having an opening;

a baffle disposed near the nozzle of the compressed air introduction pipe and the opening of the liquid suction passage;

an external air introduction pipe supported at the upper portion of the housing and extending downward into said housing; and means for adjusting the position of the baffle relative to the nozzle, said adjusting means extending through said external air introduction pipe and being supported by a threaded portion located at said upper portion.

4. The nebulizer as claimed in claim 3, wherein said adjusting means comprises a rod having threads which engage said threaded portion.

5. The nebulizer as claimed in claim 3, further comprising an air tube connected to said compressed air introduction pipe, and a compressor for feeding air to said air tube, wherein said compressor is of a linear motor driven free piston type.

6. A nebulizer, comprising:
- a housing having a liquid reservoir located at a lower portion thereof and an atomizer space and an atomized liquid discharge port located at an upper portion thereof, said atomizer space and said atomized liquid discharge port communicating with said liquid reservoir;
- a compressed air introduction pipe provided at the lower portion of the housing, said compressed air introduction pipe having a nozzle;
- a liquid suction pipe provided at the lower portion of the housing for sucking liquid in the liquid reservoir, said liquid suction pipe being removably fitted to said compressed air introduction pipe so that a liquid suction passage is formed between said liquid suction pipe and said compressed air introduction pipe, said liquid suction passage having an opening;
- a plurality of baffles disposed near the nozzle of the compressed air introduction pipe and the opening of the liquid suction passage; and
- means for adjusting the position of the baffles relative to the nozzle, said adjusting means being pivotable so that one of said baffles can be selectively placed so as to confront said nozzle.

7. The nebulizer as claimed in claim 6, further comprising a threaded portion located at said upper portion of the housing, wherein said adjusting means comprises a rod having threads which engage said threaded portion.

8. The nebulizer as claimed in claim 6, further comprising an air tube connected to said compressed air introduction pipe, and a compressor for feeding air to said air tube, wherein said compressor is of a linear motor driven free piston type.

* * * * *